United States Patent [19]

Jonas et al.

[11] Patent Number: 5,705,497
[45] Date of Patent: Jan. 6, 1998

[54] 3-ALKOXYCARBONYL-THIADIAZINONES

[75] Inventors: Rochus Jonas; Inge Lues, both of Darmstadt; Norbert Beier, Reinheim; Klaus-Otto Minck, Ober-Ramstadt, all of Germany

[73] Assignee: Merck Patent Gesellschaft mit beschrankter Haftung, Darmstadt, Germany

[21] Appl. No.: 584,127

[22] Filed: Jan. 11, 1996

[30] Foreign Application Priority Data

Jan. 11, 1995 [DE] Germany ............... 195 00 558.9

[51] Int. Cl.⁶ ............... C07D 209/02; C07D 209/56
[52] U.S. Cl. ............... 514/213; 514/223.8; 514/222.5; 544/1; 544/8
[58] Field of Search ............... 544/8, 9, 1; 514/211, 514/222.8, 222.5, 213, 223.8

[56] References Cited

U.S. PATENT DOCUMENTS

| | | |
|---|---|---|
| 4,916,128 | 4/1990 | Jonas et al. |
| 5,137,885 | 8/1992 | Jonas et al. ........... 514/222.5 |
| 5,206,363 | 4/1993 | Jonas et al. ........... 540/593 |
| 5,276,027 | 1/1994 | Jonas et al. ........... 514/222.5 |
| 5,378,702 | 1/1995 | Jonas et al. |
| 5,434,149 | 7/1995 | Jonas et al. |

FOREIGN PATENT DOCUMENTS 294647  12/1987  European Pat. Off.

OTHER PUBLICATIONS

Jonas "Preparation of the Enantiomers of the Novel Ca-Sensitizer EMD 53998", Biorganic & Medicinal Chemistry Letters, vol. 2, No. 6, pp. 589–592 (1992).

*Primary Examiner*—Jeffrey Mullis
*Attorney, Agent, or Firm*—Millen, White, Zelano, & Branigan, P.C.

[57] ABSTRACT

3-Alkoxycarbonyl thiadiazinones of the formula I

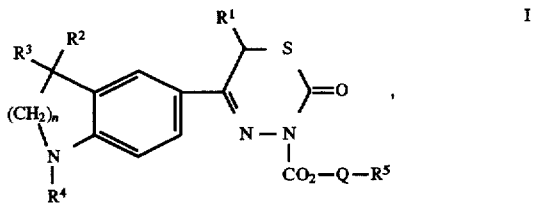

and physiologically unobjectionable salts thereof, in which $R^1$, $R^2$, $R^3$, $R^4$, $R^5$, Q and n have the meanings described herein, exhibit a positively inotropic action and can be employed for the therapy of cardiac insufficiency.

25 Claims, No Drawings

3-ALKOXYCARBONYL-THIADIAZINONES

The invention relates to novel 3-alkoxycarbonyl thiadiazinones of the formula I

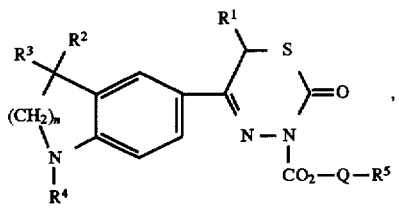

in which

R$^1$, R$^2$ and R$^3$ are each independently of one another H or A,

R$^4$ is acyl having 1 to 15 carbon atoms,

R$^5$ is NH$_2$, NHA, NA$_2$ or a saturated three- to eight-membered heterocyclic radical having at least one nitrogen atom in the ring through which the radical is bonded, which radical can be substituted by A and in which, additionally, a further CH$_2$ group in the ring can be replaced by an NH or NA group or an oxygen or sulfur atom, Q is absent or is branched or unbranched alkylene having 1 to 10 carbon atoms, n is 1, 2 or 3, and A is alkyl having 1 to 6 carbon atoms, and the physiologically acceptable salts thereof.

Thiadiazinone derivatives whose parent structure corresponds to the formula I but which otherwise have a different substitution pattern are known from DE 37 19 031 A1.

An object of the invention was to discover novel compounds having valuable properties, especially those which can be used to prepare medicaments.

Upon further study of the specification and appended claims, further objects and advantages of this invention will become apparent to those skilled in the art.

It has been found that the compounds of the formula I combine good physiological compatibility with valuable pharmacological properties. In particular, they exhibit a strong antiarrhythmic action and a positively inotropic effect. In addition, the substances have a vasodilating action and therefore promote circulation. The vasodilatory action and the antiarrhythmic action on the heart can be determined, for example, in anesthetized or conscious dogs, cats, apes or guinea pigs, and the positively inotropic action on isolated heart preparations (e.g., atrium, papillary muscle or perfused whole heart) of rats, guinea pigs, cats or dogs, for example in accordance with methods as described in Arzneimittelforschung, Volume 31 (I) No. 1a (1981), pages 141 to 170, or by Schliep et al. in 9th International Congress of Pharmacol., London, Abstracts of papers 9P (1984).

Other properties which occur are antithrombotic properties, inhibition of thrombocyte aggregation and influencing of erythrocyte form. The aggregation-inhibiting effect on the thrombocyte function can be demonstrated in the rat ex vivo in the test according to Born (Nature 194, 927–929, 1962). The antithrombotic action is evident in the prolongation of the bleeding time according to Stella (Thrombos. Res. 7, 709–716, 1975), in the reduction of the weight of thrombus in cold-induced thrombosis of the jugular vein in the rat according to Meng (Ther. Ber. 47, 69–79, 1975) and in the increase in the number of laser pulses required for complete thrombosis in the mesenteric venula of rats in accordance with a modification of the method according to Kovacs (Microvasc. Res. 6, 194–201, 1973).

The favorable effect on erythrocyte deformability can be demonstrated in the nucleopore filter in accordance with Schmid-Schönbein (Pflüger's Archiv 338, 93–114, 1973). Favorable effects can also be ascertained on the fibrinolysis/ euglobulin lysis time in accordance with v. Kaulla (Progr. Chem. Fibrinol., Thrombol. 1, 131–149, 1975; ed J. F. Davidson, Raven Press, N.Y.).

It has also been found that the introduction of alkoxycarbonyl radicals which carry basic substituents onto the thiadiazinone ring leads to readily water-soluble compounds which are of good bioavailability.

The compounds can therefore be used as active ingredients for medicaments in human and veterinary medicine. They can also be used as intermediates for the preparation of further active ingredients for medicaments.

The invention relates accordingly to the compounds of the formula I and their acid addition salts, pharmacological compositions containing them, methods of using them and to a process for their preparation.

The process is characterized in that a compound of the formula II

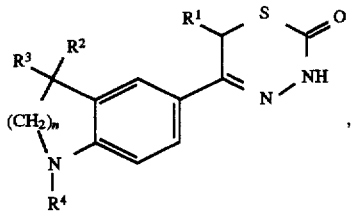

in which

R$^1$, R$^2$, R$^3$, R$^4$ and n have the meanings given, is reacted with a compound of the formula III

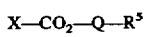

X—CO$_2$—Q—R$^5$     III, in which Q and R$^5$ have the meanings given and X is Cl, Br, OH or a reactive esterified OH group, or in that a compound of the formula IV

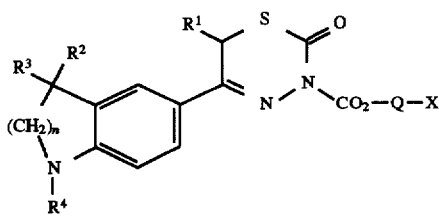

in which

R$^1$, R$^2$, R$^3$, R$^4$, n, Q and X have the meanings given, is reacted with a compound of the formula V

R$^5$—H     V, in which

R$^5$ has the meaning given, or in that a compound of the formula I but with a hydrogen atom instead of R$^4$ is acylated in a conventional manner, or in that one radical R$^4$ in a compound of the formula I is converted into another radical R$^4$, or in that a compound of the formula I in which the radical R$^5$ contains a primary or secondary amino group is alkylated in a conventional manner, and/or in that a base of the formula I is converted into one of its salts by treatment with an acid.

Above and below, the radicals $R^1$, $R^2$, $R^3$, $R^4$, $R^5$, Q and X and the index n have the meanings given in relation to the formulae I, II, III, IV and V, unless expressly stated otherwise.

In the formulae, A is preferably unbranched and preferably has 1, 2, 3 or 4 carbon atoms. Particular examples include methyl, ethyl, propyl, isopropyl, butyl, isobutyl, sec-butyl and tert-butyl, but can also preferably be n-pentyl, isopentyl, n-hexyl or isohexyl.

Q is preferably ethylene, propylene, butylene, pentylene, hexylene or, for example, 1-methylethylene.

Q—$R^5$ is preferably, in addition, N-methylpiperidyl.

The radicals $R^1$, $R^2$ and $R^3$ are preferably each H or methyl.

n is preferably 2.

$R^4$ is the acyl radical of a carboxylic or sulfonic acid, preferably alkanoyl having 1 to 10 carbon atoms, especially 1, 2, 3, 4 or 5 carbon atoms, and specifically is preferably acetyl or, also preferably, formyl, propionyl, butyryl, isobutyryl, valeryl, isovaleryl or pivaloyl (trimethylacetyl); or, also preferably, unsubstituted or substituted aroyl having 7–15 carbon atoms, suitable substituents being in particular 1–3, preferably one, of the following groups: alkyl, alkoxy, alkylthio, alkylsulfinyl or alkylsulfonyl having in each case 1–3, preferably 1 or 2, carbon atoms, methylenedioxy, and also OH, F, Cl, Br, I, $NO_2$, $NH_2$, alkylamino or dialkylamino having in each case 1–3, preferably 1 or 2, carbon atoms in the alkyl group(s). Individual preferred aroyl radicals are benzoyl, o-, m- or p-tolyl, o-, m- or p-methoxybenzoyl, 2,3-, 2,4-, 2,5-, 2,6-, 3,4- or 3,5-dimethoxybenzoyl, 2,3,4-, 2,3,5-, 2,3,6-, 2,4,5-, 2,4,6- or 3,4,5-trimethoxybenzoyl, o-, m- or p-methylthiobenzoyl, o-, m- or p-methylsulfinylbenzoyl, o-, m- or p-methylsulfonylbenzoyl, 2,3- or 3,4-methylenedioxybenzoyl or 1- or 2-naphthoyl. Acyl can additionally be heteroarylcarbonyl having 2–10 carbon atoms, such as 2- or 3-furoyl, 2- or 3-thenoyl, picolinoyl, nicotinoyl, isonicotinoyl, or arylalkanoyl such as phenylacetyl, o-, m- or p-methoxyphenylacetyl, 2- or 3-phenylpropionyl, or 2-, 3- or 4-phenylbutyryl; cycloalkylcarbonyl such as cyclohexylcarbonyl; alkylsulfonyl such as methyl-, ethyl-, propyl- or butylsulfonyl; or arylsulfonyl such as benzenesulfonyl, o-, m- or p-toluenesulfonyl, o-, m- or p-methoxybenzenesulfonyl, or 1- or 2-naphthalenesulfonyl.

The radical $R^5$ is preferably methylamino, dimethylamino, ethylamino, methylethylamino, diethylamino or pyrrolidino, piperidino or morpholino.

The invention relates in particular to those compounds of the formula I in which at least one of the above-mentioned radicals has one of the preferred meanings given above. Some preferred groups of compounds can be expressed by the following subformulae Ia to Ih, which correspond to the formula I and in which the radicals which are not designated in any more detail have the meaning given in relation to the formula I, but in which in Ia
  $R^1$ is methyl and
  n is 2;
in Ib
  $R^1$ is H and
  n is 2;
in Ic
  $R^1$ is methyl,
  $R^2$ and $R^3$ are H and
  n is 2;
in Id
  $R^1$ and $R^2$ are methyl,
  $R^3$ is H and
  n is 2;
in Ie
  $R^1$, $R^2$ and $R^3$ are methyl and
  n is 2;
in If
  $R^1$, $R^2$ and $R^3$ are methyl,
  $R^4$ is acyl having 1–10 carbon atoms and
  n is 2;
in Ig
  $R^1$ and $R^2$ are each independently of one another H or methyl,
  $R^3$ is H,
  $R^4$ is acyl having 1–10 carbon atoms,
  Q is branched or unbranched alkylene having 1–6 carbon atoms,
  $R^5$ is $NH_2$, $NHCH_3$, $NHC_2H_5$, $N(CH_3)_2$ or $N(C_2H_5)_2$, and
  n is 2;
in Ih
  $R^1$, $R^2$ and $R^3$ are methyl,
  $R^4$ is acyl having 1–10 carbon atoms and
  Q—$R^5$ is pyrrolidinoethyl, pyrrolidinopropyl, piperidinoethyl, piperidinopropyl, morpholinoethyl, morpholinopropyl, N-methylpyrrolidinyl, N-ethylpyrrolidinyl, N-methylpiperidyl, N-ethylpiperidyl or morpholinyl.

The compounds of the formula I are otherwise than described above prepared by methods which are known per se, as described in the literature (e.g., in the standard works such as Houben-Weyl, Methoden der Organischen Chemie [Methods of Organic Chemistry], Georg-Thieme Verlag, Stuttgart), specifically under reaction conditions which are known and suitable for the reactions mentioned. In this context, use can also be made of variants which are known per se and which are not mentioned in any more detail here.

The starting materials for the process claimed can if desired also be formed in situ, such that they are not isolated from the reaction mixture but are reacted further immediately to give the compounds of the formula I.

The starting materials of the formulae II and III are in some cases known. Where they are not known, they can be prepared by methods which are known per se. The preparation of the compounds of the formula II is known from DE 37 19 031.

In detail, the reaction of the compounds of the formula II with the compounds of the formula III takes place in the presence or absence of an inert solvent at temperatures of from about −20° to about +150° C., preferably from 20° to 100° C. Examples of suitable solvents are hydrocarbons such as benzene, toluene, xylenes or mesitylene; halogenated hydrocarbons such as dichloromethane, trichloroethylene or chlorobenzene; alcohols such as methanol, ethanol or isopropanol; glycols or glycol ethers such as ethylene glycol, diethylene glycol or 2-methoxyethanol; nitriles such as acetonitrile; ethers such as tetrahydrofuran or dioxane; amides such as dimethylformamide (DMF); and sulfoxides such as dimethyl sulfoxide. Mixtures of these solvents are also suitable.

In the compounds of the formula III, X is preferably Cl or Br. If X is a reactive esterified OH group, it is preferably alkylsulfonyloxy having 1–6 carbon atoms, for example methanesulfonyloxy, or arylsulfonyloxy having 6–10 carbon atoms, for example benzene-, p-toluene- or 1- or 2-naphthalenesulfonyloxy.

In addition, a compound of the formula I can also be prepared by reacting a compound of the formula IV with a compound of the formula V.

Compounds of the formula IV can be obtained by reacting a compound of the formula II with a compound of the formula Y—$CO_2$—Q—OH, in which Y is Cl, Br or a reactive esterified OH group, under conditions as indicated previously for the reaction between compounds of the formulae II and III, and by subsequently functionalizing the terminal OH group if desired.

Compounds of the formula V are known or can be prepared by methods which are known per se.

It is likewise possible to convert a radical $R^4$ into a different radical $R^4$. For example, using reactions which are known per se it is possible to etherify an OH group or to cleave an aryl ether. Furthermore, substituents of the radical $R^4$, for example S—A or SO—A groups, can be oxidized, provided the reaction takes place selectively on the radical $R^4$.

A compound of the formula I but with a hydrogen atom instead of $R^4$ can be acylated using an acyl halide of the formula $R^4$—Cl or $R^4$—Br or an anhydride of the formula $(R^4)_2O$ in an inert solvent, advantageously in the presence of a base, for example an alkali metal or alkaline earth metal hydroxide, carbonate, alcoholate or hydride, such as sodium or potassium hydroxide, carbonate, methylate, ethylate or hydride, or else a secondary or tertiary amine, for example triethylamine or pyridine.

Once obtained, a base of the formula I can be converted with an acid into the corresponding acid addition salt. Acids suitable for this reaction are those which give physiologically acceptable salts. For instance, it is possible to use inorganic acids, for example sulfuric acid, hydrohalic acids such as hydrochloric acid or hydrobromic acid, phosphoric acids such as orthophosphoric acid, nitric acid, sulfamic acid, and also organic acids, specifically aliphatic, alicyclic, araliphatic, aromatic or heterocyclic, mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- or -disulfonic acids, or laurylsulfuric acid. Salts with physiologically objectionable acids, for example picrates, can be used for purifying the compounds of the formula I.

Compounds of the formula I can contain one or more centers of asymmetry. In this case, they are usually present in racemic form. Racemates which are obtained can be separated mechanically or chemically into their enantiomers by methods which are known per se. Preferably, diastereomers are formed from the racemic mixture by reaction with an optically active separating agent. Examples of suitable separating agents for basic compounds of the formula I are optically active acids, such as the D and L forms of tartaric acid, diacetyltartaric acid, dibenzoyltartaric acid, mandelic acid, malic acid, lactic acid or the various optically active camphorsulfonic acids, such as β-camphorsulfonic acid or else optically active camphanic acid or other optically active terpene acids.

It is of course also possible to obtain optically active compounds of the formula I by the methods described above using starting materials which are already optically active.

The formula I embraces all stereoisomers and mixtures thereof, for example the racemates.

The invention relates additionally to the use of the compounds of the formula I and of their physiologically acceptable salts for the production of pharmaceutical preparations, especially by a non-chemical method. In this case, they can be brought, together with at least one solid, liquid and/or semiliquid excipient or auxiliary, and in combination if desired with one or more further active ingredients, into a suitable dosage form.

The invention also relates to compositions, especially pharmaceutical preparations, which comprise at least one compound of the formula I and/or one of its physiologically acceptable salts.

These preparations can be used as medicaments in human or veterinary medicine. Suitable excipients are organic or inorganic substances which are suitable for enteral (e.g., oral), parenteral or topical administration and which do not react with the novel compounds, examples being water, vegetable oils, benzyl alcohols, polyethylene glycols, glycerol triacetate, gelatin, carbohydrates such as lactose or starch, magnesium stearate, talc and petroleum jelly. For oral administration, use is made in particular of plain tablets, coated tablets, capsules, syrups, juices or drops; for rectal administration, of suppositories; for parenteral administration, of solutions, preferably oily or aqueous solutions, and also of suspensions, emulsions or implants; for topical administration, of ointments, creams, sticks or powders. The novel compounds can also be lyophilized and the lyophilizates obtained can be used, for example, to produce preparations for injection. The preparations indicated can be sterilized and/or can comprise auxiliaries such as lubricants, preservatives, stabilizers and/or wetting agents, emulsifiers, salts for influencing the osmotic pressure, buffer substances, colorants, flavorings and/or aroma substances. They can also if desired comprise one or more further active ingredients, for example one or more vitamins.

The compounds of the formula I can be used to combat diseases, especially arrhythmias and cases of cardiac insufficiency, and in the therapeutic treatment of the human or animal body.

In this context, the substances according to the invention are generally administered in analogy to known substances having a positively inotropic effect, such as amrinone, preferably in doses of between about 1 and 100 mg, in particular between 2 and 20 mg, per dosage unit.

The daily dose is preferably from about 0.2 to 20 mg/kg of bodyweight. The specific dose for each individual patient, however, depends on a wide variety of factors, for example the activity of the specific compound employed, the age, body weight, general state of health, sex and diet of the patient, the time and route of administration, the rate of excretion, the combination of pharmaceutical substances and the severity of the particular disease which is the subject of the therapy. Oral administration is preferred. In comparison with the digitalis glycosides used to date for the therapy of cardiac insufficiency, the compounds of the formula I are distinguished by enhanced therapeutic breadth and peripheral relief.

In the examples below, "worked up in the conventional manner" means that:

if necessary, water or dilute sodium hydroxide solution is added, the mixture is subjected to extraction with an organic solvent such as ethyl acetate, chloroform or dichloromethane, the phases are separated, the organic phase is dried over sodium sulfate, filtered and concentrated and the residue is purified by chromatography and/or crystallization. $R_f$ values on silica gel.

Above and below, all temperatures are indicated in degrees Celsius.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosure of all applications, patents and publications, cited above and below, and of corresponding German application P 195 00 558.9, filed Jan. 11, 1995, are hereby incorporated by reference.

EXAMPLES

Example 1

6 g of 2-(N,N-diethylamino)ethyl chloroformate dissolved in 50 ml of dichloromethane are added dropwise with stirring to a solution of 10 g of 3,6-dihydro-5-[1,2,3,4-tetrahydro-1-(3,4-dimethoxybenzoyl)-6-quinolyl]-6-methyl-2H-1,3,4-thiadiazin-2-one ("A") and 9.8 ml of triethylamine in 100 ml of dichloromethane, and the mixture is subsequently stirred at 20° C. for one hour. The solvent is removed, and the mixture is worked up in the conventional manner to give 3-[2-(N,N-diethylamino)ethoxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one; hydrochloride.

The following compounds are obtained by analogous reaction of "A"

with 3-(N,N-diethylamino)propyl chloroformate:

3-[3-(N,N-diethylamino)propoxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one; hydrochloride;

with 6-(N,N-dimethylamino)hexyl chloroformate:

3-[6-(N,N-dimethylamino)hexyloxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one; hydrochloride;

with 2-(N,N-dimethylamino)-1-methylethyl chloroformate:

3-[1-methyl-2-(N,N-dimethylamino)ethoxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one; hydrochloride;

with 1-methyl-4-piperidyl chloroformate:

3-(1-methyl-4-piperidyloxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one; hemifumarate;

with 2-morpholinoethyl chloroformate:

3-(2-morpholinoethoxycarbonyl)-5-[1,2,3,4-tetrahydro-1(3,4-dimethoxybenzoyl)-6-quinolyl]-6-methyl-3,6-dihydro-2H-1,3,4-thiadiazin-2-one;

with 3-morpholinopropyl chloroformate:

3-(3-morpholinopropoxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one;

with 2-thiomorpholinoethyl chloroformate:

3-(2-thiomorpholinoethoxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one;

with 3-thiomorpholinopropyl chloroformate:

3-(3-thiomorpholinopropoxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one;

with 2-piperazinoethyl chloroformate:

3-(2-piperazinoethoxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one;

with 3-piperazinopropyl chloroformate:

3-(3-piperazinopropoxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one;

with 2-pyrrolidinoethyl chloroformate:

3-(2-pyrrolidinoethoxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one;

with 3-pyrrolidinopropyl chloroformate:

3-(3-pyrrolidinopropoxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one.

The following compounds are obtained analogously by reacting (+)-3,6-dihydro-5-[1,2,3,4-tetrahydro-1-(3,4-dimethoxybenzoyl)-6-quinolyl]-6-methyl-2H-1,3,4-thiadiazin-2-one with 2-(N,N-diethylamino)ethyl chloroformate:

(+)-3-[2-(N,N-diethylamino)ethoxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one; hydrochloride, m.p. 135;

with 3-(N,N-diethylamino)propyl chloroformate:

(+)-3-[3-(N,N-dimethylamino)propoxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one; hydrochloride, m.p. 130;

with 6-(N,N-diethylamino)hexyl chloroformate:

(+)-3-[6-(N,N-dimethylamino)hexyloxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one; hydrochloride, m.p. 133;

with 6-(N,N-diethylamino)-1-methylethyl chloroformate:

(+)-3-[1-methyl-2-(N,N-dimethylamino)ethoxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one; hydrochloride, m.p. 168;

with 1-methyl-4-piperidyl chloroformate:

(+)-3-(1-methyl-4-piperidyloxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one; hydrochloride, m.p. 150;

The following compounds are obtained analogously by reacting 2-(N,N-diethylamino) ethyl chloroformate with 5-[1,2,3,4-tetrahydro-1-(3-ethoxy-4-methoxybenzoyl)-6-quinolyl]-6-methyl-3,6-dihydro-2H-1,3,4-thiadiazin-2-one:

3-[2-(N,N-diethylamino)ethoxycarbonyl]-5-[1,2,3,4-tetrahydro-1-(3-ethoxy-4-methoxybenzoyl)-6-quinolyl]-6-methyl-3,6-dihydro-2H-1,3,4-thiadiazin-2-one;

with 5-[1,2,3,4-tetrahydro-1-(3-methoxy-4-ethoxybenzoyl)-6-quinolyl]-6-methyl-3,6-dihydro-2H-1,3,4-thiadiazin-2-one:

3-[2-(N,N-diethylamino)ethoxycarbonyl]-5-[1,2,3,4-tetrahydro-1-(3-methoxy-4-ethoxybenzoyl)-6-quinolyl]-6-methyl-3,6-dihydro-2H -1,3,4-thiadiazin-2-one;

with 5-[1,2,3,4-tetrahydro-1-(3-methoxy-4-hydroxybenzoyl)-6-quinolyl]-6-methyl-3,6-dihydro-2H-1,3,4-thiadiazin-2-one:

3-[2-(N,N-diethylamino)ethoxycarbonyl]-5-[1,2,3,4-tetrahydro-1-(3-methoxy-4-hydroxybenzoyl)-6-quinolyl]-6-methyl-3,6-dihydro-2H-1,3,4-thiadiazin-2-one.

Example 2

6 g of 2-(N,N-diethylamino)ethyl chloroformate dissolved in 50 ml of dichloromethane are added dropwise with stirring to a solution of 10 g of 3,6-dihydro-5-[1,2,3,4-tetrahydro-1-(3,4-dimethoxybenzoyl)-4,4-dimethyl-6-quinolyl]-6-methyl-2H-1,3,4-thiadiazin-2-one ("B") and 9.8 ml of pyridine in 100 ml of dichloromethane and the mixture is subsequently stirred at 20° C. for one hour. The solvent is removed and the mixture is worked up in the conventional manner to give 3-[2-(N,N-diethylamino)ethoxycarbonyl]-5-[1,2,3,4-tetrahydro-1-(3,4-dimethoxybenzoyl)-4,4-dimethyl-6-quinolyl]-6-methyl-3,6-dihydro-2H-1,3,4-thiadiazin-2-one; $R_f$ (THF) 0.65.

The following compounds are obtained by analogous reaction of "B"

with 3-(N,N-diethylamino)propyl chloroformate:

3-[3-(N,N-diethylamino)propoxycarbonyl]-5-[1,2,3,4-tetrahydro-1-(3,4-dimethoxybenzoyl)-4,4-dimethyl-6-quinolyl]-6-methyl-3,6-dihydro-2H-1,3,4-thiadiazin-2-one; $R_f$ (THF) 0.64;

with 6-(N,N-dimethylamino)hexyl chloroformate:

3-[6-(N,N-dimethylamino)hexyloxycarbonyl]-5-[1,2,3,4-tetrahydro-1-(3,4-dimethoxybenzoyl)-4,4-dimethyl-6-quinolyl]-6-methyl-3,6-dihydro-2H-1,3,4-thiadiazin-2-one; $R_f$ (THF) 0.2;

with 2-(N,N-dimethylamino)-1-methylethyl chloroformate:

3-[1-methyl-2-(N,N-dimethylamino) ethoxycarbonyl]-5-[1,2,3,4-tetrahydro-1-(3,4-dimethoxybenzoyl)-4,4-dimethyl-6-quinolyl]-6-methyl-3,6-dihydro-2H-1,3,4-thiadiazin-2-one; $R_f$ (THF) 0.25;

with 1-methyl-4-piperidyl chloroformate:

3-(1-methyl-4-piperidyloxycarbonyl)-5-[1,2,3,4-tetrahydro-1-(3,4-dimethoxybenzoyl)-4,4-dimethyl-6-quinolyl]-6-methyl-3,6-dihydro-2H-1,3,4-thiadiazin-2-one; hemifumarate; $R_f$ (THF) 0.65.

The following are obtained analogously by reacting 2-(N,N-diethylamino) ethyl chloroformate with 5-[1,2,3,4-tetrahydro-1-(3-ethoxy-4-methoxybenzoyl)-6-quinolyl]-4,4-dimethyl-6-methyl-3,6-dihydro-2H-1,3,4-thiadiazin-2-one:

3-[2-(N,N-diethylamino)ethoxycarbonyl]-5-[1,2,3,4-tetrahydro-1-(3-ethoxy-4-methoxybenzoyl)-4,4-dimethyl-6-quinolyl]-6-methyl-3,6-dihydro-2H-1,3,4-thiadiazin-2-one;

with 5-[1,2,3,4-tetrahydro-1-(3-methoxy-4-ethoxybenzoyl)-6-quinolyl]-4,4-dimethyl-6-methyl-3,6-dihydro-2H-1,3,4-thiadiazin-2-one:

3-[2-(N,N-diethylamino)ethoxycarbonyl]-5-[1,2,3,4-tetrahydro-1-(3-methoxy-4-ethoxybenzoyl)-4,4-dimethyl-6-quinolyl]-6-methyl-3,6-dihydro-2H-1,3,4-thiadiazin-2-one;

with 5-[1,2,3,4-tetrahydro-1-(3-methoxy-4-hydroxybenzoyl)-4,4-dimethyl-6-quinolyl]-6-methyl-3,6-dihydro-2H-1,3,4-thiadiazin-2-one:

3-[2-(N,N-diethylamino)ethoxycarbonyl]-5-[1,2,3,4-tetrahydro-1-(3-methoxy-4-hydroxybenzoyl)-4,4-dimethyl-6-quinolyl]-6-methyl-3,6-dihydro-2H-1,3,4-thiadiazin-2-one.

Example 3

2.5 g of diethylamine dissolved in 30 ml of dichloromethane are added dropwise with stirring to a solution of 10 g of 3-[2-chloroethoxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one and 9 ml of pyridine in 100 ml of dichloromethane and the mixture is subsequently stirred at 20° C. for one hour. The solvent is removed and the mixture is worked up in the conventional manner to give 3-[2-(N,N-diethylamino)ethoxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one; hydrochloride.

Example 4

The following compounds are obtained in analogy to Example 1 by reacting 3-(N,N-diethylamino)propyl chloroformate with 5-[1,2,3,4-tetrahydro-1-(3-ethoxy-4-methoxybenzoyl)-6-quinolyl]-6-methyl-3,6-dihydro-2H-1,3,4-thiadiazin-2-one:

3-[3-(N,N-diethylamino)-propoxycarbonyl]-5-[1,2,3,4-tetrahydro-1-(3-ethoxy-4-methoxybenzoyl)-6-quinolyl]-6-methyl-3,6-dihydro-2H-1,3,4-thiadiazin-2-one;

with 5-[1,2,3,4-tetrahydro-1-(3-methoxy-4-ethoxybenzoyl)-6-quinolyl]-6-methyl-3,6-dihydro-2H-1,3,4-thiadiazin-2-one:

3-[3-(N,N-diethylamino)propoxycarbonyl]-5-[1,2,3,4-tetrahydro-1-(3-methoxy-4-ethoxybenzoyl)-6-quinolyl]-6-methyl-3,6-dihydro-2H-1,3,4-thiadiazin-2-one;

with 5-[1,2,3,4-tetrahydro-1-(3-methoxy-4-hydroxybenzoyl)-6-quinolyl]-6-methyl-3,6-dihydro-2H-1,3,4-thiadiazin-2-one:

3-[3-(N,N-diethylamino)propoxycarbonyl]-5-[1,2,3,4-tetrahydro-1-(3-methoxy-4-hydroxybenzoyl)-6-quinolyl]-6-methyl-3,6-dihydro-2H-1,3,4-thiadiazin-2-one.

Example 5

The following compounds are obtained in analogy to Example 2 by reacting 3-(N,N-diethylamino)propyl chloroformate with 5-[1,2,3,4-tetrahydro-1-(3-ethoxy-4-methoxybenzoyl)-4,4-dimethyl-6-quinolyl]-6-methyl-3,6-dihydro-2H-1,3,4-thiadiazin-2-one:

3-[3-(N,N-diethylamino)propoxycarbonyl]-5-[1,2,3,4-tetrahydro-1-(3-ethoxy-4-methoxybenzoyl)-4,4-dimethyl-6-quinolyl]-6-methyl-3,6-dihydro-2H-1,3,4-thiadiazin-2-one;

with 5-[1,2,3,4-tetrahydro-1-(3-methoxy-4-ethoxybenzoyl)-4,4-dimethyl-6-quinolyl]-6-methyl-3,6-dihydro-2H-1,3,4-thiadiazin-2-one:

3-[3-(N,N-diethylamino)-propoxycarbonyl]-5-[1,2,3,4-tetrahydro-1-(3-methoxy-4-ethoxybenzoyl)-4,4-dimethyl-6-quinolyl]-6-methyl-3,6-dihydro-2H-1,3,4-thiadiazin-2-one;

with 5-[1,2,3,4-tetrahydro-1-(3-methoxy-4-hydroxybenzoyl)-4,4-dimethyl-6-quinolyl]-6-methyl-3,6-dihydro-2H-1,3,4-thiadiazin-2-one:

3-[3-(N,N-diethylamino)propoxycarbonyl]-5-[1,2,3,4-tetrahydro-1-(3-methoxy-4-hydroxybenzoyl)-4,4-dimethyl-6-quinolyl]-6-methyl-3,6-dihydro-2H-1,3,4-thiadiazin-2-one.

Example 6

5 ml of triethylamine and then, dropwise with stirring, 4 ml of acetyl chloride are added to a solution of 12 g of 3-[2-(N,N-diethylamino)ethoxycarbonyl]-5-(1,2,3,4-tetrahydro-6-quinolyl)-6-methyl-3,6-dihydro-2H-1,3,4-thiadiazin-2-one [obtainable in analogy to Example 1 by reacting 5-(1,2,3,4-tetrahydro-6-quinolyl)-6-methyl-3,6-dihydro-2H-1,3,4-thiadiazin-2-one with 2-(N,N-diethylamino)ethyl chloroformate] in 100 ml of dichloromethane. The mixture is subsequently stirred at 20° C. for one hour and decomposed with water and the mixture is worked up in the conventional manner to give 3-[2-(N,N-diethylamino)ethoxycarbonyl]-5-(1-acetyl-1,2,3,4-tetrahydro-6-quinolyl)-6-methyl-3,6-dihydro-2H-1,3,4-thiadiazin-2-one.

The following 3-[2-(N,N-diethylamino)-ethoxycarbonyl]-6-methyl-3,6-dihydro-2H-1,3,4-thiadiazin-2-ones are obtained analogously:

5-(1-Formyl-1,2,3,4-tetrahydro-6-quinolyl)-
5-(1-Propionyl-1,2,3,4-tetrahydro-6-quinolyl)-
5-(1-Butyryl-1,2,3,4-tetrahydro-6-quinolyl)-
5-(1-Isobutyryl-1,2,3,4-tetrahydro-6-quinolyl)-
5-(1-Valeryl-1,2,3,4-tetrahydro-6-quinolyl)-
5-(1-Isovaleryl-1,2,3,4-tetrahydro-6-quinolyl)-
5-(1-Pivaloyl-1,2,3,4-tetrahydro-6-quinolyl)-
5-(1-Benzoyl-1,2,3,4-tetrahydro-6-quinolyl)-
5-(1-p-Methoxybenzoyl-1,2,3,4-tetrahydro-6-quinolyl)-
5-[1-(3,4-Methylenedioxybenzoyl)-1,2,3,4-tetrahydro-6-quinolyl]-
5-(1-p-Methylthiobenzoyl-1,2,3,4-tetrahydro-6-quinolyl)-
5-(1-p-Methylsulfinylbenzoyl-1,2,3,4-tetrahydro-6-quinolyl)-
5-(1-p-Methylsulfonylbenzoyl-1,2,3,4-tetrahydro-6-quinolyl)-
5-(1-Picolinoyl-1,2,3,4-tetrahydro-6-quinolyl)-
5-(1-Nicotinoyl-1,2,3,4-tetrahydro-6-quinolyl)-
5-(1-Isonicotinoyl-1,2,3,4-tetrahydro-6-quinolyl)-
5-(1-Methanesulfonyl-1,2,3,4-tetrahydro-6-quinolyl)-
5-(1-Benzenesulfonyl-1,2,3,4-tetrahydro-6-quinolyl)-
5-(1-p-Toluenesulfonyl-1,2,3,4-tetrahydro-6-quinolyl)-
5-(1-Formyl-4,4-dimethyl-1,2,3,4-tetrahydro-6-quinolyl)-
5-(1-Acetyl-4,4-dimethyl-1,2,3,4-tetrahydro-6-quinolyl)-
5-(1-Propionyl-4,4-dimethyl-1,2,3,4-tetrahydro-6-quinoyl)-
5-(1-Butyryl-4,4-dimethyl-1,2,3,4-tetrahydro-6-quinolyl)-
5-(1-Isobutyryl-4,4-dimethyl-1,2,3,4-tetrahydro-6-quinolyl)-
5-(1-Valeryl-4,4-dimethyl-1,2,3,4-tetrahydro-6-quinolyl)-
5-(1-Isovaleryl-4,4-dimethyl-1,2,3,4-tetrahydro-6-quinolyl)-
5-(1-Pivaloyl-4,4-dimethyl-1,2,3,4-tetrahydro-6-quinolyl)-
5-(1-Benzoyl-4,4-dimethyl-1,2,3,4-tetrahydro-6-quinolyl)-
5-(1-p-Methoxybenzoyl-4,4-dimethyl-1,2,3,4-tetrahydro-6-quinolyl)-
5-(1-(3,4-Methylenedioxybenzoyl)-4,4-dimethyl-1,2,3,4-tetrahydro-6-quinolyl)-
5-(1-p-Methylthiobenzoyl-4,4-dimethyl-1,2,3,4-tetrahydro-6-quinolyl)-
5-(1-p-Methylsulfinylbenzoyl-4,4-dimethyl-1,2,3,4-tetrahydro-6-quinolyl)-
5-(1-p-Methylsulfonylbenzoyl-4,4-dimethyl-1,2,3,4-tetrahydro-6-quinolyl)-
5-(1-Picolinoyl-4,4-dimethyl-1,2,3,4-tetrahydro-6-quinolyl)-
5-(1-Nicotinoyl-4,4-dimethyl-1,2,3,4-tetrahydro-6-quinolyl)-
5-(1-Isonicotinoyl-4,4-dimethyl-1,2,3,4-tetrahydro-6-quinolyl)-
5-(1-Methanesulfonyl-4,4-dimethyl-1,2,3,4-tetrahydro-6-quinolyl)-
5-(1-Benzenesulfonyl-4,4-dimethyl-1,2,3,4-tetrahydro-6-quinolyl)-
5-(1-p-Toluenesulfonyl-4,4-dimethyl-1,2,3,4-tetrahydro-6-quinolyl)-.

Example 7

The following compounds are obtained in analogy to Example 1 by reacting
3,6-dihydro-5-[1,2,3,4-tetrahydro-1-(3-methoxy-4-ethoxybenzoyl)-6-quinolyl]-6-methyl-2H-1,3,4-thiadiazin-2-one with 3-morpholinopropyl chloroformate:

3-(3-morpholinopropoxycarbonyl)-5-[1,2,3,4-tetrahydro-1-(3-methoxy-4-ethoxybenzoyl)-6-quinolyl]-6-methyl-2H-1,3,4-thiadiazin-2-one;

3,6-dihydro-5-[1,2,3,4-tetrahydro-1-(3-methoxy-4-ethoxybenzoyl)-6-quinolyl]-6-methyl-2H-1,3,4-thiadiazin-2-one with 3-piperidinopropyl chloroformate:

3-(3-piperidinopropoxycarbonyl)-5-[1,2,3,4-tetrahydro-1-(3-methoxy-4-ethoxybenzoyl)-6-quinolyl]-6-methyl-2H-1,3,4-thiadiazin-2-one.

Example 8

1.3 g of ethyl chloride dissolved in 10 ml of toluene are added dropwise with stirring to a solution of 10 g of 3-(3-piperazinopropoxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one and 1.8 g of triethylamine in 100 ml of toluene, and the mixture is stirred with heating for one hour. The solvent is removed and the mixture is worked up in the conventional manner to give 3-[3-(1-ethyl-4-piperazinyl)-propoxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one.

Example 9

The following compounds are obtained in analogy to Example 1 by reacting
3,6-dihydro-5-[1,2,3,4-tetrahydro-1-(3-methoxy-4-ethoxybenzoyl)-4,4-dimethyl-6-quinolyl]-6-methyl-2H-1,3,4-thiadiazin-2-one with 3-morpholinopropyl chloroformate:

3-(3-morpholinopropoxycarbonyl)-5-[1,2,3,4-tetrahydro-1-(3-methoxy-4-ethoxybenzoyl)-4,4-dimethyl-6-quinolyl]-6-methyl-3,6-dihydro-2H-1,3,4-thiadiazin-2-one;

3,6-dihydro-5-[1,2,3,4-tetrahydro-1-(3-methoxy-4-ethoxybenzoyl)-4,4-dimethyl-6-quinolyl]-6-methyl-2H-1,3,4-thiadiazin-2-one with 3-piperidinopropyl chloroformate:

3-(3-piperidinopropoxycarbonyl)-5-[1,2,3,4-tetrahydro-1-(3-methoxy-4-ethoxybenzoyl)-4,4-dimethyl-6-quinolyl]-6-methyl-3,6-dihydro-2H-1,3,4-thiadiazin-2-one;

3,6-dihydro-5-[1,2,3,4-tetrahydro-1-(3,4-dimethoxybenzoyl)-6-quinolyl]-6-methyl-2H-1,3,4-thiadiazin-2-one with Cl—C(=O)—O—$C_{10}H_{20}$—N$(CH_3)_2$:

3-[10-(N,N-dimethylamino)decyloxycarbonyl]-5-[1,2,3,4-tetrahydro-1-(3,4-dimethoxybenzoyl)-6-quinolyl]-6-methyl-3,6-dihydro-2H-1,3,4-thiadiazin-2-one, m.p. 87° C.;

3,6-dihydro-5-[1,2,3,4-tetrahydro-1-(3,4-dimethoxybenzoyl)-6-quinolyl]-6-methyl-2H-1,3,4-thiadiazin-2-one with 6-pyrrolidinohexyl chloroformate:

3-(6-pyrrolidinohexyloxycarbonyl)-5-[1,2,3,4-tetrahydro-1-(3,4-dimethoxybenzoyl)-6-quinolyl]-6-methyl-3,6-dihydro-2H-1,3,4-thiadiazin-2-one. m.p. 107° C.

The examples which follow relate to pharmaceutical preparations which comprise active ingredients of the formula I or salts thereof.

Example A

Plain and coated tablets

Tablets having the following composition are pressed in a conventional manner and if desired are coated with a customary sucrose-based coating:

| Active ingredient of the formula I | 100 mg |
|---|---|
| Microcrystalline cellulose | 278.8 mg |
| Lactose | 110 mg |
| Corn starch | 11 mg |
| Magnesium stearate | 5 mg |
| Finely divided silica | 0.2 mg |

Example B

Hard gelatin capsules

Customary two-part hard gelatin capsules are each filled with

| Active ingredient of the formula I | 100 mg |
|---|---|
| Lactose | 150 mg |
| Cellulose | 50 mg |
| Magnesium stearate | 6 mg |

Example C

Soft gelatin capsules

Customary soft gelatin capsules are filled with a mixture of in each case 50 mg of active ingredient and 250 mg of olive oil.

Example D

Ampoules

A solution of 200 g of active ingredient in 2 kg of 1,2-propanediol is made up to 10 l with water and is used to fill ampoules such that each ampoule contains 20 mg of active ingredient.

Example E

Aqueous suspension for oral administration

An aqueous suspension of the active ingredient is prepared in a conventional manner. The unit dose (5 ml) contains 100 mg of active ingredient, 100 mg of Na carboxymethyl cellulose, 5 mg of Na benzoate and 100 mg of sorbitol.

Example F

Suppositories

A mixture of 20 g of active ingredient is melted with 100 g of soya lecithin and 1400 g of cocoa butter, poured into molds and allowed to cool. Each suppository contains 20 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 3-alkoxycarbonylthiadiazinone compound of the formula I

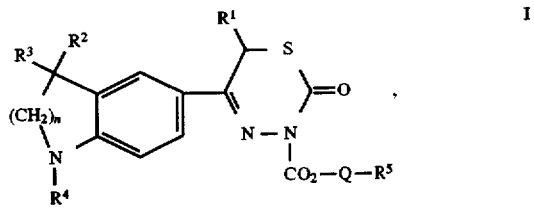

in which $R^1$, $R^2$ and $R^3$ are each independently of one another H or A, $R^4$ is an acyl radical of a carboxylic or sulfonic acid having 1 to 15 carbon atoms, $R^5$ is $NH_2$, NHA, $NA_2$ or a saturated three- to eight-membered heterocyclic radical having at least one nitrogen atom in the ring through which the radical is bonded, which radical can be substituted by A and in which, additionally, a further $CH_2$ group in the ring can be replaced by an NH or NA group or an oxygen or sulfur atom, Q is absent or is branched or unbranched alkylene having 1 to 10 carbon atoms, n is 1, 2 or 3, and A is alkyl having 1 to 6 carbon atoms, and the physiologically acceptable salts thereof.

2. An enantiomer of an optically active compound of the formula I according to claim 1.

3. A compound of formula I of claim 1, being:

a) 3-[2-(N,N-Diethylamino)ethoxycarbonyl]-5-[1,2,3,4-tetrahydro-1-(3,4-dimethoxybenzoyl)-6-quinolyl]-6-methyl-2H-3,6-dihydro-1,3,4-thiadiazin-2-one;

b) 3-[3-(N,N-diethylamino)propoxycarbonyl]-5-[1,2,3,4-tetrahydro-1-(3,4-dimethoxybenzoyl)-6-quinolyl]-6-methyl-2H-3,6-dihydro-1,3,4-thiadiazin-2-one;

c) 3-[6-(N,N-dimethylamino)hexyloxycarbonyl]-5-[1,2,3,4-tetrahydro-1-(3,4-dimethoxybenzoyl)-6-quinolyl]-6-methyl-2H-3,6-dihydro-1,3,4-thiadiazin-2-one;

d) 3-[1-methyl-2-(N,N-dimethylamino)ethoxycarbonyl]-5-[1,2,3,4-tetrahydro-1-(3,4-dimethoxybenzoyl)-6-quinolyl]-6-methyl-2H-3,6-dihydro-1,3,4-thiadiazin-2-one;

e) 3-[1-methyl-4-piperidyloxycarbonyl]-5-[1,2,3,4-tetrahydro-1-(3,4-dimethoxybenzoyl)-6-quinolyl]-6-methyl-2H-3,6-dihydro-1,3,4-thiadiazin-2-one;

f) 3-[2-(N,N-diethylamino)ethoxycarbonyl]-5-[1,2,3,4-tetrahydro-1-(3,4-dimethoxybenzoyl)-4,4-dimethyl-6-quinolyl]-6-methyl-2H-3,6-dihydro-1,3,4-thiadiazin-2-one;

g) 3-[6-(N,N-dimethylamino)hexyloxycarbonyl]-5-[1,2,3,4-tetrahydro-1-(3,4-dimethoxybenzoyl)-4,4-dimethyl-6-quinolyl]-6-methyl-2H-3,6-dihydro-1,3,4-thiadiazin-2-one;

(h) 3-[1-methyl-4-piperidyloxycarbonyl]-5-[1,2,3,4-tetrahydro-1-(3,4-dimethoxybenzoyl)-4,4-dimethyl-6-quinolyl]-6-methyl-2H-3,6-dihydro-1,3,4-thiadiazin-2-one;

(i) 3-[1-methyl-2-(N,N-dimethylamino)-ethoxycarbonyl]-5-[1,2,3,4-tetrahydro-1-(3,4-dimethoxybenzoyl)-4,4-dimethyl-6-quinolyl]-6-methyl-2H-3,6-dihydro-1,3,4-thiadiazin-2-one;

or an enantiomer thereof.

4. A process for the preparation of compounds of the formula I according to claim 1 and of salts thereof, comprising reacting a compound of the formula II

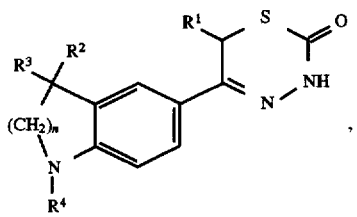

in which $R^1$, $R^2$, $R^3$, $R^4$ and n have the meanings already given, with a compound of the formula III:

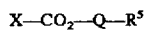

X—CO$_2$—Q—R$^5$  III, in which $R^5$ and Q have the meanings given and

X is Cl, Br, OH or a reactive esterified OH group, or reacting a compound of the formula IV

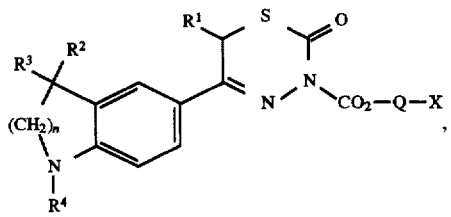

in which $R^1$, $R^2$, $R^3$, $R^4$, Q, n and X have the meanings already given, with a compound of the formula V

R$^5$—H  V, in which $R^5$ has the meanings already given, or alkylating a compound of the formula I having a primary or a secondary amino group as $R^5$ to obtain a compound wherein $R^5$ is a secondary or tertiary amino group in a conventional manner, or acylating a compound, which would be of the formula I except it has a hydrogen atom instead of the radical $R^4$, to replace the hydrogen atom with an $R^4$ radical in a conventional manner, or converting one radical $R^4$ in a compound of the formula I into another radical $R^4$, and/or converting a base of the formula I into one of its salts by treatment with an acid.

5. A process for the production of pharmaceutical preparations, comprising combining a compound of the formula I according to claim 1 and/or one of its physiologically acceptable salts together with at least one solid, liquid or semiliquid excipient or auxiliary, into a suitable dosage form.

6. A pharmaceutical preparation, comprising at least one compound of the formula I according to claim 1 or a physiologically acceptable salts thereof.

7. The compound of claim 1, wherein n is 2.

8. The compound of claim 1, wherein $R^4$ is an acyl radical of a carboxylic or sulfonic acid of 1–15 carbon atoms.

9. The compound of claim 1, wherein $R^5$ is amino, methylamino, dimethylamino, ethylamino, methylethylamino, diethylamino, pyrrolidino, piperidino, morpholino, N-methylpyrrolidino, N-ethylpyrrolidino, N-methylpiperidyl or N-ethylpiperidyl.

10. The compound of claim 1, wherein $R^1$, $R^2$ and $R^3$ are independently hydrogen or methyl.

11. The compound of claim 1, wherein Q is branched or unbranched alkylene of 1–6 carbon atoms.

12. A method for treatment or prevention of disease which comprises administering to a patient in need thereof an effective amount of a compound or physiologically acceptable salt of claim 1.

13. The method of claim 12, wherein the disease is arrhythmia.

14. The method of claim 13, wherein the compound or physiologically acceptable salt is administered in a daily dose of 0.2 to 20 mg/kg of body weight.

15. The method of claim 12, wherein the compound or physiologically acceptable salt is administered to provide a positive inotropic effect.

16. The method of claim 15, wherein the compound or physiologically acceptable salt is administered in a daily dose of 0.2 to 20 mg/kg of body weight.

17. The method of claim 12, wherein the compound or physiologically acceptable salt is administered in a daily dose of 0.2 to 20 mg/kg of body weight.

18. A compound of claim 1, wherein $R^1$ is methyl and n is 2.

19. A compound of claim 1, wherein $R^1$ is H and n is 2.

20. A compound of claim 1, wherein $R^1$ is methyl, $R^2$ and $R^3$ are H and n is 2.

21. A compound of claim 1, wherein $R^1$ and R are methyl, $R^3$ is H and n is 2.

22. A compound of claim 1, wherein $R^1$, $R^2$ and $R^3$ are methyl and n is 2.

23. A compound of claim 1, wherein $R^1$, $R^2$ and $R^3$ are methyl, $R^4$ is the acyl radical of a carboxylic or sulfonic acid having 1–10 carbon atoms and n is 2.

24. A compound of claim 1, wherein $R^1$ and $R^2$ are each independently of one another H or methyl, $R^3$ is H, $R^4$ is the acyl radical of a carboxylic or sulfonic acid having 1–10 carbon atoms, Q is branched or unbranched alkylene having 1–6 carbon atoms, $R^5$ is $NH_2$, $NHCH_3$, $NHC_2H_5$, $N(CH_3)_2$ or $N(C_2H_5)_2$, and n is 2.

25. A compound of claim 1, wherein $R^1$, $R^2$ and $R^3$ are methyl, $R^4$ is the acyl radical of a carboxylic or sulfonic acid having 1–10 carbon atoms and Q—$R^5$ is pyrrolidinoethyl, pyrrolidinopropyl, piperidinoethyl, piperidinopropyl, morpholinoethyl, morpholinopropyl, N-methylpyrrolidinyl, N-ethylpyrrolidinyl, N-methylpiperidyl, N-ethylpiperidyl or morpholinyl.

* * * * *